United States Patent [19]

Oksman et al.

[11] Patent Number: 5,118,401
[45] Date of Patent: Jun. 2, 1992

[54] APPARATUS FOR DISINFECTING AN INSTRUMENT

[76] Inventors: Henry C. Oksman, 20 Wagon Wheel Rd., Mamaroneck, N.Y. 10543; Joseph Eisner, 219 E. 32nd St., New York, N.Y. 10016

[21] Appl. No.: 532,624

[22] Filed: Jun. 4, 1990

[51] Int. Cl.⁵ .................. C25B 9/00; C25B 15/08; A61M 1/00
[52] U.S. Cl. .................. 204/228; 204/229; 204/271; 204/275; 222/319; 222/405; 424/613; 424/615; 424/616; 604/118; 604/187; 604/218
[58] Field of Search ........ 204/228, 271, 278, 275–277, 204/224 R, 1.11 R; 604/218, 118, 187; 424/613, 615, 616; 514/840; 222/319, 405

[56] References Cited

U.S. PATENT DOCUMENTS

| | | | |
|---|---|---|---|
| 1,004,369 | 9/1911 | Ciolfi | 204/275 X |
| 2,082,845 | 6/1937 | Osborne | 222/319 X |
| 2,293,922 | 8/1942 | Serinis | 222/319 X |
| 2,498,129 | 2/1950 | Lindsay | 204/224 R |
| 3,346,477 | 10/1967 | Wolfer | 204/224 R |
| 3,814,941 | 6/1974 | Czaplinski | 604/218 |
| 3,819,329 | 6/1974 | Kaestner et al. | 204/128 X |
| 3,996,126 | 12/1976 | Rasmussen | 204/278 X |
| 4,512,865 | 4/1985 | Yamauchi | 204/271 |
| 4,560,455 | 12/1985 | Porth et al. | 204/271 X |
| 4,687,997 | 8/1987 | Tao | 204/32.1 X |
| 4,839,004 | 6/1989 | Castellini | 204/271 X |
| 4,889,689 | 12/1989 | Tsao | 424/616 X |
| 4,986,820 | 1/1991 | Fischer | 604/218 |
| 4,986,963 | 1/1991 | Corcoran et al. | 424/613 X |

FOREIGN PATENT DOCUMENTS

| | | | |
|---|---|---|---|
| 0077502 | 4/1983 | European Pat. Off. | 424/616 |
| 0155505 | 9/1985 | European Pat. Off. | 514/840 |

Primary Examiner—Donald R. Valentine
Attorney, Agent, or Firm—Howard F. Mandelbaum

[57] ABSTRACT

Apparatus for applying a disinfectant solution which may include hydrogen peroxide, a salt and a buffer to an instrument wherein the instrument can be inserted into an opening in the wall of a vessel containing a disinfectant normally at a level below the opening. A floatation plunger is urged downwardly to displace the disinfectant to a level in engagement with the instrument and the electrodes are energized to activate the disinfectant. A magnetic latch holds the floatation plunger in place during disinfection and the disinfectant level is sensed to enable energization of the electrodes only when the level is sufficient to engage the instrument.

24 Claims, 4 Drawing Sheets

APPARATUS FOR DISINFECTING AN INSTRUMENT

BACKGROUND OF THE INVENTION

There has long been a need for disinfecting medical instruments between applications to the body, particularly in sensitive areas, e.g. the eyes, in order to prevent transmission of disease causing bacteria and viruses. Recent isolation of immunodeficiency virus from tears of patients with AIDS and the isolation of Herpes Simplex virus type one, Hepatitis B virus and Adenovirus has heightened interest in the transmission of these diseases. Herpes Simplex Viral eye disease is a leading cause of corneal blindness in the United States and other industrialized nations, as well as developing countries throughout the world. Herpetic eye disease in the United States occurs in about one half million people per year. Ten million people are estimated to be affected annually worldwide and several million people are visually impaired as a result of Herpetic eye disease. Trachoma, caused by a chlamydial organism is a chronic and progressive infectious disease which is the world's leading cause of preventable blindness. It is a potential contaminant of ocular instruments worldwide.

Bacteria such as Staphylococcus, Pseudomonas, Bacillus, Pneumococci and Acanthamoeba are serious causes of ocular infections. Common fungi such as Fusarium Solani, Aspergillus Fumigatus and Candida Albicans contribute to a large number of fungal infections. All are potential agents for contaminating ocular instruments during routine examinations.

There is increased pathogenic flora in contact lens wearers, thus raising the potential for instrument contamination whenever such patients are being examined. The number of reported cases of Acanthamoeba Keratitis has increased dramatically in recent years. These organisms are known to exhibit a propensity to adhere to the walls of plastic containers, thereby being potential contaminants in ophthalmological settings.

The American Academy of Ophthalmology recommends soaking tonometer heads in a dilute Clorox solution. Alcide Corporation developed a two compound product called Exspor that has to be mixed and then diluted. This chlorous acid based chemical sterilizes within three minutes and disinfects spores only after the disinfected article is soaked in the solution for six hours. Another commonly used disinfectant is three percent hydrogen peroxide. It destroys spores when the disinfected article is soaked for four hours. An alternate agent is seventy percent isopropyl alcohol wipes, recommended for preventing possible transmission of viruses from tears, via tonometers.

Present methods for disinfecting non metallic ocular instruments are cumbersome and time consuming both in preparation and implementation. The chemical solutions used are toxic and in some cases require special precautions in order to prevent any potential risk of chemical residue getting into the eye. For example, fluffy white corneal lesion was seen in a patient immediately after applanation tonometry. The tonometer applanation surface had been disinfected with peroxide solution overnight. Slit-lamp examination revealed a circular corneal epithelial defect corresponding in size to the tonometer applanation surface. In another case, damage to the cornea was a result of wiping the tonometer with seventy percent isopropyl alcohol. After using the applanation tonometer, slit-lamp examination of a thirty-eight year old woman with type I diabetes mellitus revealed a circular area of corneal epithelial opacification corresponding to the size of the tonometer applanation surface.

SUMMARY OF THE INVENTION

The present invention overcomes the aforementioned disadvantages of the prior art by teaching the construction of an apparatus for applying a disinfectant to an instrument, e.g., a tonometer. More specifically, The present invention teaches the construction of an apparatus for applying a disinfectant to an instrument comprising a vessel for receiving the disinfectant having an opening in a side wall for removably mounting the instrument in fluid tight engagement with the wall, a seal mounted in the opening for preventing the disinfectant from flowing through the opening when the instrument is mounted therein, a sensor mounted on the vessel adjacent the opening for signaling when the instrument is received in the opening, a floatation plunger at least partially freely disposed within the vessel for movement relative thereto, and having a bore wherethrough the disinfectant can flow into the vessel, whereby the floatation plunger may be moved between a first position at which the disinfectant is at a first level below the instrument when it is mounted in the opening and a second position at which disinfectant within the vessel is displaced to a second level to envelop the face of the instrument when mounted in the wall, first and second spaced electrodes disposed in the vessel for generating an electrolysis current in the disinfectant, means connected to said electrodes for generating a leakage current therebetween only when the disinfectant is at a level sufficient to cover the instrument to be disinfected and the electrodes, a latch mounted on at least one of the floatation plunger and the vessel for fixing the floatation plunger with respect to the vessel when the latch is engaged and for enabling the floatation plunger to freely move with respect to the vessel when the latch is disengaged, a valve for draining the disinfectant from the vessel, a timed current switch operatively connected to the electrodes for enabling the electrolysis current to flow for a predetermined period of time, the timed current switch being operatively connected to the latch for enabling the timed current switch to commence the predetermined period of time in response to engagement of the latch, and operatively connected to the sensor for enabling the electrolysis current to flow only when the instrument is received in the wall opening and the disinfectant is at the second level, an event counter operatively connected to the timed current switch for counting the number of the periods of time, and signaling means operatively connected to the event counter for providing an indication when a predetermined number of the time periods have elapsed.

It is therefore an object of the invention to provide an apparatus for disinfection of an instrument which can provide a high degree of clinical compliance in a user friendly system.

Another object of the invention is to provide an apparatus for disinfection of an instrument with a solution that is rendered nontoxic and non-pathogenic after disinfection.

Still another object of the invention is to provide an apparatus for disinfection of an instrument having a disinfection period limited to several minutes.

Still a further object of the invention is to provide an apparatus for disinfection of an instrument which informs the operator of the progress and completion of a successful disinfection cycle.

An additional object of the invention is to provide an apparatus for disinfection of an instrument which informs the operator of the requirement to change the disinfectant after a predetermined number of cycles or a predetermined time period.

Other and further objects of the invention will be apparent from the following drawings and description of a preferred embodiment of the invention in which like reference numerals are used to indicate like parts in the various views.

DESCRIPTION OF THE PREFERRED EMBODIMENTS

The invention utilizes a device including an electrolytic cell where current flows for a designated period of time, preferably one to five minutes. The tonometer applanation surface is inserted into the device and disinfected within a short period, leaving no toxic residues or chemicals on the applanation surface.

Aqueous sodium chloride (normal saline) with three percent hydrogen peroxide is a commonly used disinfectant. When this solution is used in an electrolytic cell, reduction reactions at the cathode deliver free electrons. This results in the formation of very reactive free radicals that increase the disinfection potential of the solution.

Although generation of free radicals, specifically superoxides, is increased by the presence of hydrogen peroxide in an electrolytic solution, peroxide is not essential, as superoxide will form in the electrolysis of normal saline without peroxide. During the electrolysis of a purely saline solution, with or without peroxide, chlorine gas escapes, sodium hydroxide concentration increases and pH rises. For disinfecting an instrument intended to contact the eye, it is important for additional nonelectrolyzable solutes to be added to the solution and the amount of saline reduced. The relative proportion of solutes determines the concentration of free radicals and other ions generated under given voltage-current conditions. Two of the acceptable non electrolyzable solutes are NaI or $Na_2SO_4$.

The power (P) delivered to an electrolytic cell is the product of the applied voltage (V) multiplied by the current (I) passing between the electrodes:

$$P = V*I$$

Current is dependent on the concentration of conductive electrolytic ions in solution, the distance between electrodes (d) and the applied voltage (V). Another important factor is the ionization potential. As the voltage to the cell is increased the strength of the electric field (E) generated is increased according to $$E = V/d$$

Ionization potential is directly proportional to electric field strength. As the applied voltage is increased additional species of solution constituents ionize. Ion concentration can, hence, be controlled by varying the applied voltage. When hydrogen peroxide is present, a greater number of superoxide ions are generated.

If the time required for a ten fold reduction in viability, referred to as the "D Value," is too long more free radicals and other ions are needed. These can be increased either by raising current or voltage input. Increasing power input affects electrode surface current density and its degradation. It also increases the species generated. At very high field values even the stable solutes will electrolyze. Therefore voltage-current values can be changed within a limited range. Another method to add more free radicals is to increase either NaCl concentration, peroxide concentration, or concentration of other electrolyzable salts.

The disinfection system of the invention utilizes common disinfectants such as $Cl_2$, $I_2$, $O_2$, $H_2O_2$, NaOH or other ions as desired. A significant contribution to the disinfection process is the generation of very specific, short lived disinfectant ions or free radicals.

Figures 1, 2:
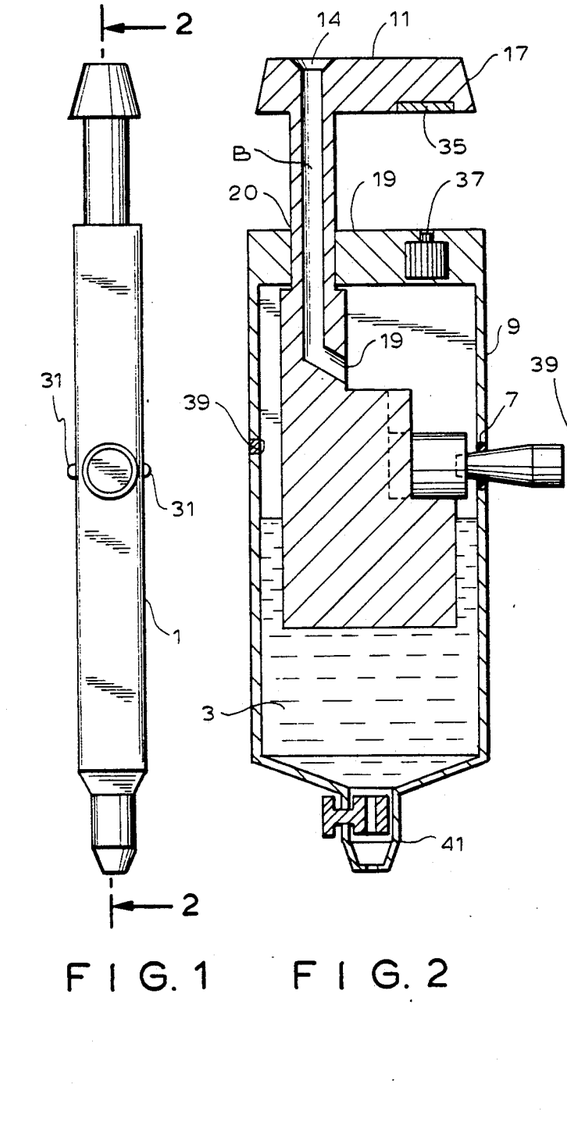
FIG. 1 is a front elevation view of the apparatus of the preferred embodiment of the invention.
FIG. 2 is a side sectional elevation view of the apparatus of the preferred embodiment of the invention in a first disposition.
Figure 3:
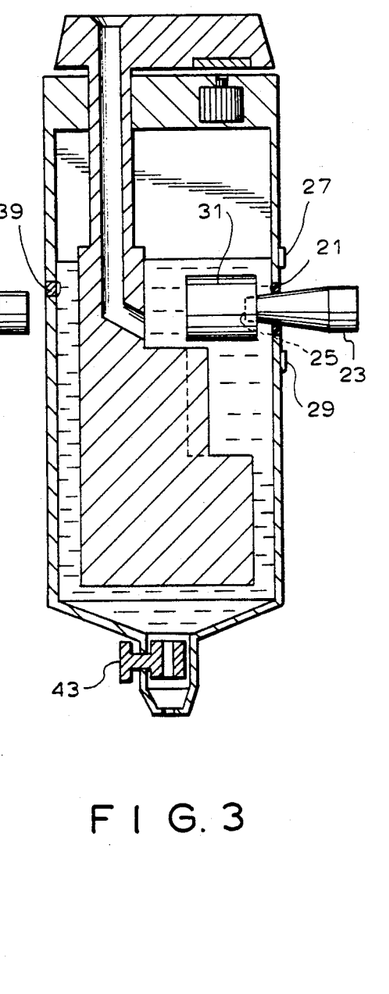
FIG. 3 is a side sectional elevation view of the apparatus of the preferred embodiment of the invention in a second disposition.

Referring now to FIGS. 1, 2 and 3 of the drawings there is shown a disinfection system for disinfecting the applanation surface of a tonometer. It will be apparent that other instruments may be similarly disinfected.

The disinfection system includes a hollow vessel 1 of rectangular cross section which can be attached to a slit-lamp by a swing arm (not shown). The vessel 1 is partially filled with a disinfectant solution 3 below opening 7 in vessel wall 9. A floatation plunger 11 having a bore 13 with an inlet 14 in a plunger handle portion 17 thereof and an plunger outlet 19 near the top of a stepped portion of the floatation plunger 11 floats freely in the disinfectant solution 3. The vessel 1 has a cover 19 with an aperture 20 congruent to a uniform cross section of an elongated length of the floatation plunger 11.

The disinfectant solution 3 is preferably composed of a solution containing from zero to five percent hydrogen peroxide and conductive electrolytic salts. The salt composition can be chosen from a variety of compounds such as NaCl, $Na_2SO_4$, $CaSO_4$, NaI and KBr. In order to avoid large pH variations a buffer is also desired. Phosphate buffers, e.g., $NaH_2PO_4$, $Na_2HPO_4$ or $Na_3PO_4$ are stable under electrolysis and can be added to limit pH variations. For use with tonometers or any other instrument intended to contact the eye, solution tonicity should be in a range between half to twice isotonic concentration. However, in order to enhance disinfection, the tonicity of the solution is desirably at least ten percent (10%) above or below isotonic concentration. That is, it is desirable that the solution tonicity be in the range from 50% to 90% of isotonic concentration or from 110% to 200% of isotonic concentration. The solute composition necessary to maintain tonicity in this range is a function of the physical layout of the electrolytic cell, electrode sizes, composition of other solution constituents, and the applied voltage or current.

Circumscribing the opening 7 in the vessel wall 9 is an O-ring seal 21 having an inner circumference equal to the outer circumference of a portion of the frustoconical housing of a tonometer 23 for removably mounting the tonometer 23 in the opening 7 with the tonometer applanation surface 25 disposed within the vessel 1. Also mounted on the vessel wall 9 adjacent the opening 7 and in diametric opposition are a photodiode 27 and a photodetector 29 directed toward one another so that light emitted by the photodiode 27 impinges upon the photodetector 29 except when a tonometer 23 is mounted in the opening 7 of the vessel wall 9, at which time the tonometer 23 obstructs the light path between the photodiode 27 and photodetector 29 so that no detectable light is received by the photodetector 29.

Also mounted on opposite sides of the vessel walls 9 at no less than the same elevation as the opening 7 in the wall 9 are cell electrodes 31 between which a current can be conducted through the disinfectant solution 3. The cell electrodes 31 should have poorly oxidizing properties, yet act as catalysts in the electrolysis of peroxide and other ions. Heavy metals such as palladium, rhodium, platinum and the like have excellent properties for this purpose.

Disinfectant solution 3 is added to the vessel 1 in a quantity sufficient to rise above the opening 7 in the vessel wall 9 when the floatation plunger 11 is moved downward to the point where a latch ferromagnetic pole piece 35 in the plunger handle 17 engages a latch electromagnet 37 mounted in the vessel cover 19. Fluid level sensor 39 is mounted in the vessel 1 and detects a difference in electrical potential in the solution caused by flow of a leakage current between the electrodes 31 when they are covered with the disinfectant solution 3, i.e., when the level of the disinfectant solution 3 is above the opening 7 in the vessel wall 9, and above the tonometer applanation surface 25 of the tonometer 23 mounted in the opening 7.

The vessel 1 is fitted with a spout 41 on its underside in which there is mounted a normally closed spigot 43 which can be opened to drain the disinfectant solution 3 from the vessel 1.

Figure 5:
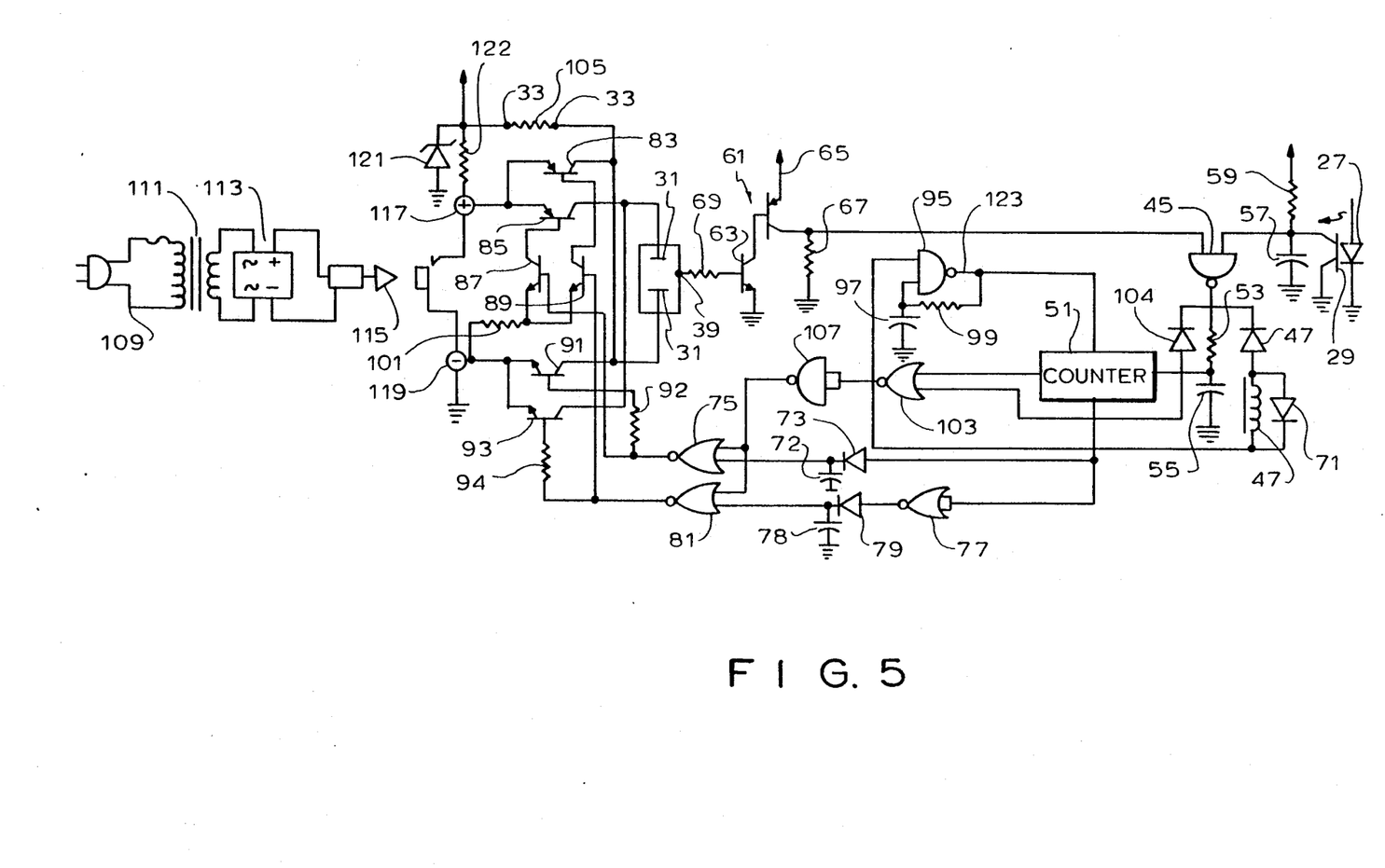
FIG. 5 is a schematic circuit diagram of the apparatus of the preferred embodiment of the invention.

Referring additionally to FIG. 5 of the drawings wherein the control circuitry 2 is shown, the photodiode 27 directs light across the opening 7 which is sensed by the photodetector 29. The photodetector 29 is connected to one input of a NAND gate 45 which receives a low signal from the photodetector 29 in the absence of a tonometer 23 in the opening 7 of the vessel wall 9. This results in a high signal at the output of the NAND gate 45, which biases a diode 47 to prevent current flow to the inductor 49 of the latch electromagnet 37. The high output of the NAND gate 45 is applied to the reset input of a counter 51 via an RC network including resistor 53 and capacitor 55 to keep it in the reset condition and unable to count. Following a power outage, the system is reset by the RC network composed of capacitor 57 and resistor 59 when electric power is restored by applying a signal to the NAND gate 45.

The other input of the NAND gate 45 is connected to the output of an amplifier 61 which is formed by transistor 63, transistor 65 and resistor 67. Resistor 69 applies a signal from fluid level sensor 39 to the input of amplifier 61 only when the level of the disinfectant solution 3 is above the electrodes 31. When the level of the disinfectant solution 3 is below the electrodes 31, the output signal from the NAND gate 45 is low. This also results in a high signal at the output of the NAND gate 45 which biases the diode 47 to prevent current flow to the inductor 49 of the latch electromagnet 37 and keeps the counter 51 reset and unable to count. A diode 71 in parallel with inductor 49 deenergizes the latch electromagnet 37 at the end of the cycle.

The amplifier 61 formed by transistor 63, transistor 65 and resistor 67 applies a high signal to the other input of NAND gate 45 when the solution 3 is above the tonometer opening 7. When the disinfectant solution 3 is above the opening 7 and the tonometer 23 is mounted in the opening 7, the output of NAND gate 45 goes low, thereby enabling the counter 51 to count and the latch electromagnet 37 to be energized to attract the latch ferromagnetic pole piece 35.

When enabled, counter 51 periodically changes the logical level of its output signal which is conducted through diode 73 to NOR gate 75 at predetermined times, e.g., 8 times during the disinfection cycle, and at the same time, the signal is inverted in inverter 77 and then conducted through diode 79 to nor gate 81. When the output of diode 73 is high, the output of diode 78 is low and vice versa. The capacitor 72 and diode 73, and the capacitor 78 and diode 79 ensure that before the signal goes high at each respective line there will be a delayed low signal. This delay ensures that the current in the chamber will be turned off before it changes polarity. Otherwise an electrical short is possible. Hence, while, the counter 51 is counting, the polarity of the current in the cell reverses resulting in a square wave having a period determined by the selected count output of the counter 51. Transistors 83, 85, 87, 89, 91, and 93 switch the current direction between the cell electrodes 31. The frequency at which the cell electrodes 31 change polarity is determined by the frequency of an oscillator 123 composed of NAND gate 95, capacitor 97 and resistor 99 in conjunction with the counter 51. The oscillator 123 provides high frequency pulses to the clock input of the counter 51.

The sensor amplifier 61 transmits a signal to the electronic circuit regarding solution level status. The presence of the tonometer cylinder is continuously monitored by the photodiode 27 and photodetector 29.

When the output of NOR gate 75 is high it enables transistor 87, transistor 91 and transistor 85 to be turned on for positive square wave current between the cell electrodes 31. When the output of NOR gate 81 is high it enables transistor 89, transistor 93 (through resistor 94), and transistor 83 to be turned on for negative square wave current between the cell electrodes 31. The inverter 77 keeps the square wave current in phase during cycling of the alternating voltage.

When the alternating input voltage is positive, transistor 91 is turned on via resistor 92. At the same time, transistor 87 conducts current from the base of transistor 85 via resistor 101 to ground thereby turning transistor 85 on. At this time transistors 93, 89, and 83 are off thereby causing current to flow through the cell from top electrode to bottom electrode in the orientation of FIG. 5.

When the output of counter 51 is low, transistors 91, 87, and 86 are turned off and, correspondingly, transistors 93, 89, and 83 are turned on thereby causing the current to flow through the cell from bottom electrode to top electrode in the orientation of FIG. 5.

At the end of the cycle, the counter 51 times out and outputs a signal which is conducted to one input of inverter 103, the other input of which is connected to the output of NAND gate 45 through resistor 105. When either the cycle has ended or the tonometer 23 is out of the opening 7, the output of inverter 103 goes low causing output of inverter 107 to go high. This in turn causes the outputs of NOR gate 75 and NOR gate 81 to remain low preventing transistors 87 and 89 from turning on so that no current flows in the cell between the cell electrodes 31. In this way the counter 51 acts as a timed current switch to allow current to flow between the cell electrodes 31 for a predetermined period of time.

A plug 109 connected to a standard wall outlet supplies AC power to a transformer 111 where the voltage is stepped down and then rectified by a rectifier 113. The resulting DC voltage is then applied, via a connector 115 across terminal 117 and terminal 119 where it is regulated by a Zener diode 121 connected to a resistor 122. The transformer 111 and rectifier energize the cell electrodes 31.

A resistor 105 provides a leakage current through the electrodes 31 to enable the fluid level to be detected when it rises to a level submerging the electrodes 31 and the tonometer applanation surface 25.

If the tonometer 23 is out of the vessel wall opening 7, or the level of the disinfectant solution 3 is low, i.e., below electrodes 31, a low signal at the output of NAND gate 45 deenergizes the electromagnet coil 49 and resets the counter 51.

In use, a predetermined quantity of disinfectant solution 3 is poured into the vessel 1 preferably, although not necessarily, through the bore 13 in the plunger 11. The quantity is such as to be below the opening 7 in the wall 9 when the plunger 11 is upwardly disposed or entirely out of the vessel 1 and to rise above the opening 7 when the plunger 11 is fully inserted into the vessel 1. Before full insertion of the plunger 11, a tonometer 23 is mounted in the opening 7 of the vessel wall 9.

The operator then presses the plunger handle 17 to push the floatation plunger 11 into the disinfectant solution 3, thereby causing the fluid level to rise above the opening 7 and the tonometer applanation surface 25. The latch electromagnet 37 holds the latch ferromagnetic pole piece 35 and the plunger handle 17 down for the duration of the disinfection cycle. During the disinfection cycle the solution level is above the tonometer applanation surface 25 and forms an electrolytic conducting interface between the cell electrodes 31. At the end of the disinfection cycle the latch electromagnet 37 releases the plunger handle 17 allowing the floatation plunger 11 to rise and the solution level to move down to its original level. At this time the tonometer applanation surface 25 and the cell electrodes 31 are no longer immersed in disinfectant solution 3 and the tonometer applanation surface 25 is disinfected and ready for use.

Whenever the fluid level is insufficient, the latch electromagnet 37 and latch ferromagnetic pole piece 35 will not latch and a message to that effect can be made to appear on a display. After a predetermined number of uses or a given period of time, used solution can be removed through the spout 41 and replacement solution poured through the plunger inlet 14.

Figure 6:
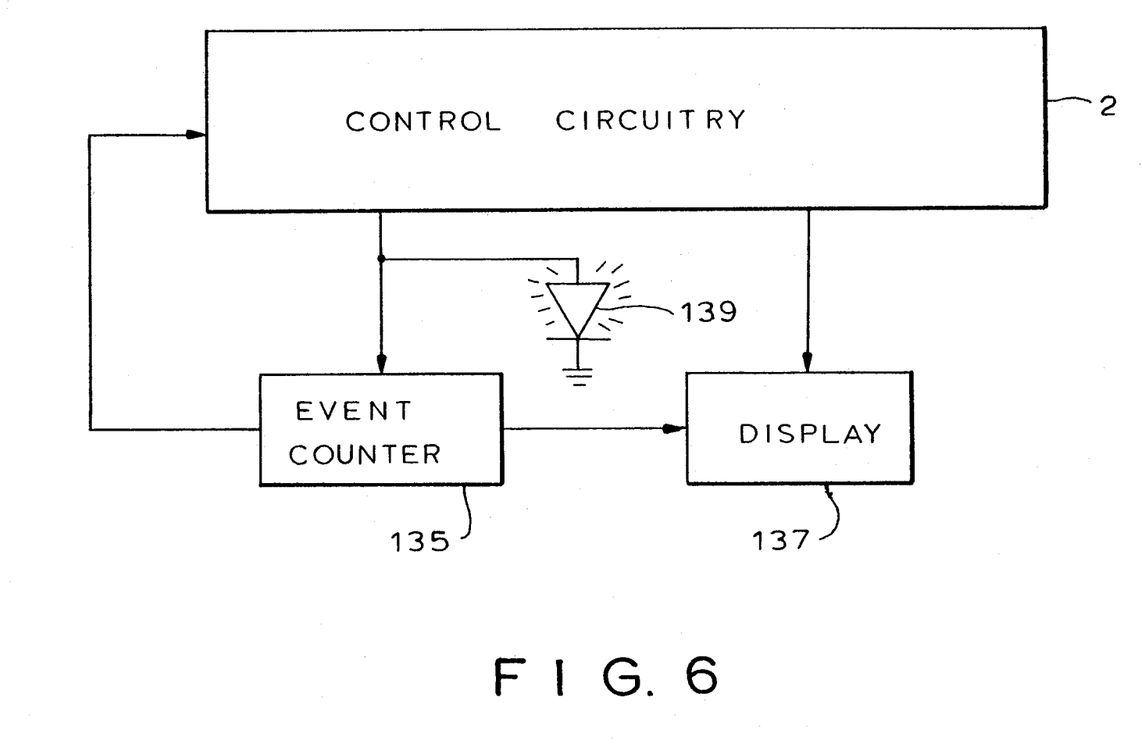
FIG. 6 is a block diagram of the apparatus for monitoring and reporting on the status of the process of the preferred embodiment of the invention.

Referring now to FIG. 6, there is shown, in block diagram form, an event counter 135 for counting the number of instrument disinfection cycles and a display 137 for displaying appropriate instructive messages. The circuitry employed for counting and display is conventional and will be known to those skilled in the art.

The display 137 presents alphanumeric information regarding system disinfection status. At the termination of the disinfection cycle an indicator, e.g., a green light, which can be an L.E.D. 139, can signal completion of cycle and a ready message can be displayed on the display 137.

Each time a disinfection cycle is completed, a count in the event counter 135 can be incremented. The count can then be compared with a predetermined maximum number of cycles. For example, the above described disinfection fluid should be used only for a limited number of operations e.g., approximately 30 c.c. for the sooner of for 50 disinfection cycles or an elapsed time of one week. The counter 135 can count the number of cycles. After 50 cycles have been completed, an alphanumeric message can be displayed on the display 137 signaling that the solution should be replaced.

Figure 4:
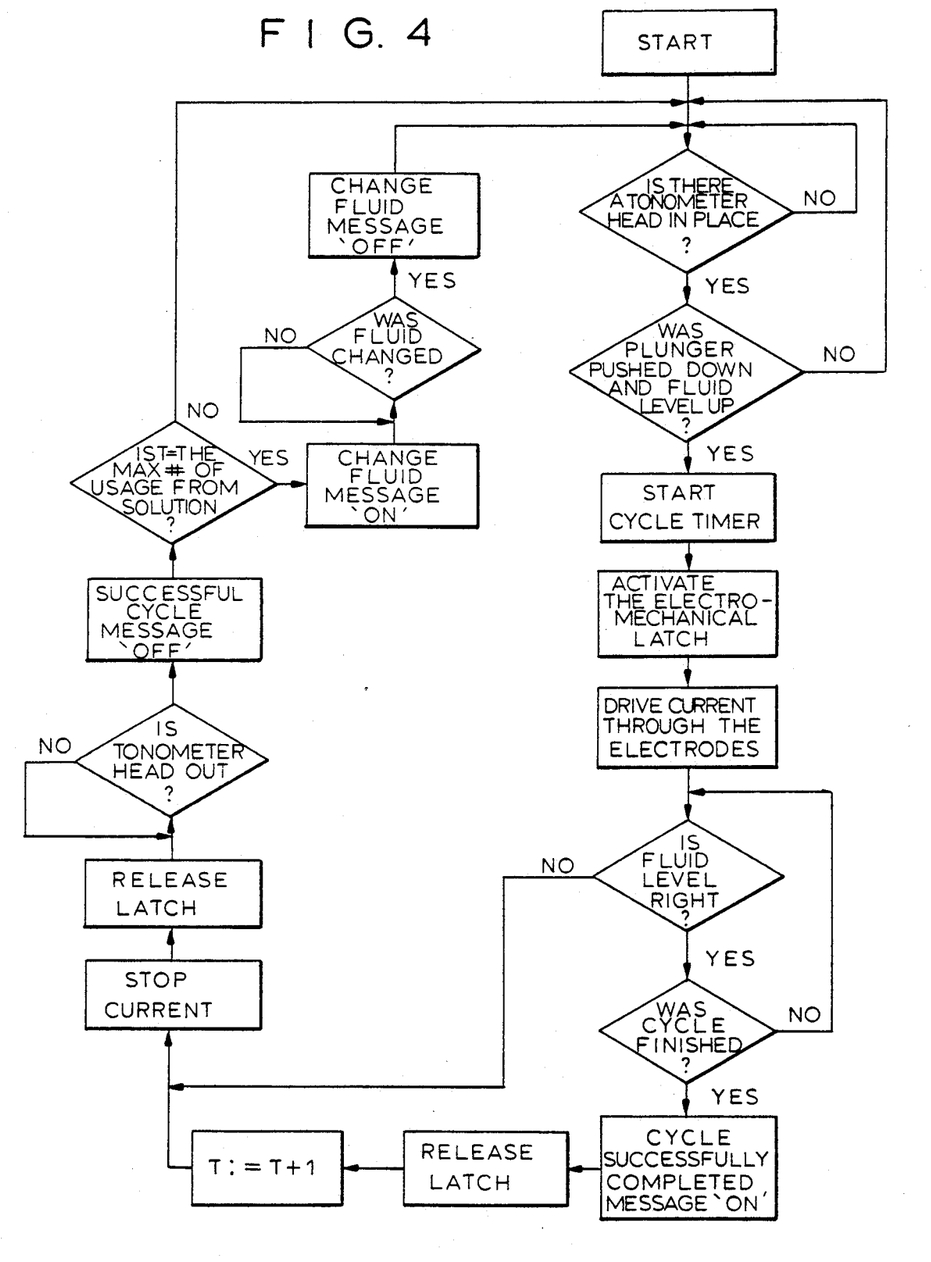
FIG. 4 is a flow diagram illustrating the sequence of operation of the preferred embodiment of the invention.

Referring to FIG. 4 there is shown a logic flow diagram for the electronics of the apparatus. At power on, the photodiode 27 and photodetector 29 determine whether a tonometer 23 is mounted in the opening 7 of the vessel wall 9 and whether the disinfectant solution 3 is above the electrodes 31 and, hence, the tonometer 23. Only if both conditions prevail does the counter 51 begin its cycle. The latch ferromagnetic pole piece 35 is then latched to the latch electromagnet 37 to hold the plunger handle 17 down.

The system then continuously checks whether the disinfecant solution 3 is above the electrodes 31 and whether the output of the counter 51 indicates an end of the cycle. Successful completion of the cycle can cause an appropriate message to that effect to be displayed, e.g., by lighting an L.E.D. or by displaying a message on an L.E.D. or L.C.D. display. In addition, the latch ferromagnetic pole piece 35 is deenergized to release the floatation plunger 11 and a cycle counter is incremented by one. If the fluid level should drop below the electrodes 31 prior to completion of the cycle governed by the counter 51, no indication of a successful completion is given nor is the cycle counter incremented.

After the tonometer 23 is removed from the vessel 1 and the level of the disinfectant solution 3 drops below the electrodes 31, the successful cycle message is turned off. A determination is then made as to whether the disinfectant solution 3 is due to be changed by comparing the count in the cycle counter with a predetermined stored representation of a number corresponding to the maximum number of permissible cycles for a charge of disinfectant solution 3. Alternatively a clock may be used to measure elapsed time since the last change of disinfectant solution 3. When the maximum number of cycles is reached or the elapsed time reaches the time for a change of disinfectant solution 3, a change fluid message is displayed. The system is initialized and ready for a new cycle provided that a change of disinfectant solution 3 is done when required.

As previously mentioned, the disinfection unit can be mounted on a slit lamp, whereby the tonometer can be easily swung into position, such that the tip is received in the device. Once the tonometer is in the vessel, the handle is pressed to initiate disinfection.

It is to be appreciated that the foregoing is a description of a preferred embodiment of the invention to which variations and modifications may be made without departing from the spirit and scope of the invention. For example, not only tonometers, but other medical and nonmedical instruments may be disinfected according to the teachings of the invention. In addition, the time periods stated above can be varied.

What is claimed is:

1. Apparatus for applying a solution capable of being rendered disinfecting to an instrument comprising
    a vessel for receiving said solution having a wall with an opening for receiving said instrument in fluid tight engagement with said wall,
    a floatation plunger insertable into said vessel for movement relative thereto between a first position at which a quantity of said disinfectant can be at a first level below said instrument when it is received in said opening and a second position at which said disinfectant quantity within said vessel is displaced by said plunger to a second level to envelop at least a portion of said instrument when received in said wall,
    a pair of electrodes mounted within said vessel for, when energized, rendering said solution disinfecting and/or neutralizing said solution after it is rendered disinfecting, and
    energizing means connected to said electrodes and responsive to the position of said plunger with respect to said vessel for energizing said electrodes when said plunger is in said second position.

2. Apparatus for applying a disinfectant to an instrument according to claim 1 wherein said opening is in a side wall of said vessel and further comprising a seal mounted therein for preventing said disinfectant from flowing through said opening while said instrument is received therein.

3. Apparatus for applying a disinfectant to an instrument according to claim 2 wherein said floatation plunger has one region outside of said vessel and another region inside of said vessel and a bore extending between said first and second regions whereby said disinfectant can be inserted into said vessel through said bore.

4. Apparatus for applying a disinfectant to an instrument according to claim 1 further comprising leakage current means mounted in said vessel for causing a leakage current to flow in said solution when contained therein, and sensor means for detecting said leakage current, said energizing means being responsive to said sensor means for energizing said electrodes only when said leakage current is above a predetermined threshold.

5. Apparatus for applying a disinfectant to an instrument according to claim 4 wherein said leakage current means is connected to said electrodes for causing said leakage current to flow therebetween.

6. Apparatus for applying a disinfectant to an instrument according to claim 1 further comprising a latch mounted on at least one of said floatation plunger and said vessel for fixing said floatation plunger with respect to said vessel when said latch is engaged and for enabling said floatation plunger to freely move with respect to said vessel when said latch is disengaged.

7. Apparatus for applying a disinfectant to an instrument according to claim 6 wherein said latch is connected to said sensor means for being engaged only when said leakage current threshold is exceeded.

8. Apparatus for applying a disinfectant to an instrument according to claim 6 wherein said energizing means comprises a timed current switch for enabling said electrolysis current to flow for a predetermined period of time.

9. Apparatus for applying a disinfectant to an instrument according to claim 8 wherein said timed current switch is operatively connected to said latch for enabling said timed current switch to commence said predetermined period of time in response to engagement of said latch.

10. Apparatus for applying a disinfectant to an instrument according to claim 9 further comprising an event counter operatively connected to said timed current switch for counting the number of said periods of time, and signaling means operatively connected to said event counter for providing an indication when a predetermined number of said periods have passed.

11. Apparatus for applying a disinfectant to an instrument according to claim 1 further comprising an instrument sensor mounted on said vessel adjacent said opening for signaling when said instrument is received in said opening, said energizing means being operatively connected to said instrument sensor for energizing said electrodes only when an instrument is disposed in said opening.

12. An instrument disinfection apparatus comprising
    a vessel having a wall with an opening for receiving said instrument,
    an ionizable liquid, contained with said vessel, and
    a floatation plunger insertable into said vessel for displacing said liquid to envelop a region within said vessel adjacent said opening.

13. An instrument disinfection apparatus according to claim 12 further comprising a pair of electrodes mounted within said vessel for rendering said solution disinfecting and/or neutralizing said solution after it is rendered disinfecting.

14. An instrument disinfection apparatus according to claim 13 further comprising energizing means for energizing said electrodes.

15. An instrument disinfection apparatus according to claim 14 further comprising fluid level sensing means for generating a signal when said fluid is in said region adjacent said opening, said energizing means being responsive to said fluid level sensing means signal for energizing said electrodes only when said fluid level sensing means signal indicates that said fluid is in said region.

16. An instrument disinfection apparatus according to claim 14 further comprising a latch mounted on at least one of said floatation plunger and said vessel for fixing said floatation plunger with respect to said vessel when said latch is engaged and for enabling said floatation plunger to freely move with respect to said vessel when said latch is disengaged.

17. An instrument disinfection apparatus according to claim 16 wherein said latch is connected to said instrument sensor for being engaged only when said instrument is disposed in said opening.

18. An instrument disinfection apparatus according to claim 12 wherein said liquid comprises from zero to five percent hydrogen peroxide and a conductive electrolytic salt.

19. An instrument disinfection apparatus according to claim 18 wherein said conductive electrolytic salt is selected from the group consisting of $NaCl$, $Na_2SO_4$, $CaSO_4$, $NaI$ and $KBr$.

20. An instrument disinfection apparatus according to claim 18 further comprising a buffer.

21. An instrument disinfection apparatus according to claim 20 wherein said buffer is a phosphate buffer.

22. An instrument disinfection apparatus according to claim 21 wherein said buffer is selected from the group consisting of $NaH_2PO_4$, $Na_2HPO_4$ and $Na_3PO_4$.

23. An instrument disinfection apparatus according to claim 12 wherein said liquid has a solution tonicity in a range from half to twice isotonic concentration.

24. An instrument disinfection apparatus according to claim 12 wherein said ionizable liquid comprises a solution capable of being rendered disinfecting for sterilizing an instrument comprising from zero to five percent hydrogen peroxide and a conductive electrolytic salt, said solution having a tonicity in the range from 50% to 90% of isotonic concentration of from 110% to 200% of isotonic concentration.

* * * * *

UNITED STATES PATENT AND TRADEMARK OFFICE
CERTIFICATE OF CORRECTION

PATENT NO. : 5,118,401
DATED : JUNE 2, 1992
INVENTOR(S) : OKSMAN ET AL.

It is certified that error appears in the above-identified patent and that said Letters Patent is hereby corrected as shown below:

At column 12, line 5, change "of" to --or--.

Signed and Sealed this

Fourteenth Day of September, 1993

Attest:

BRUCE LEHMAN

*Attesting Officer*    *Commissioner of Patents and Trademarks*